United States Patent [19]

Sano et al.

[11] 4,220,516
[45] Sep. 2, 1980

[54] OXYGEN SENSOR

[75] Inventors: Hiromi Sano, Nagoya; Masatoshi Suzuki, Kariya, both of Japan

[73] Assignee: Nippondenso Co., Ltd., Kariya, Japan

[21] Appl. No.: 1,354

[22] Filed: Jan. 4, 1979

[30] Foreign Application Priority Data

Jan. 17, 1978 [JP] Japan .................................. 53-3568

[51] Int. Cl.$^2$ ............................................ G01N 27/58
[52] U.S. Cl. ................................................ 204/195 S
[58] Field of Search ............................ 204/1 S, 195 S

[56] References Cited

U.S. PATENT DOCUMENTS

| 3,978,006 | 8/1976 | Topp et al. | 204/195 S |
| 3,989,614 | 11/1976 | Tien | 204/195 S |
| 4,076,608 | 2/1978 | Fujishiro et al. | 204/195 S |
| 4,101,403 | 7/1978 | Kita et al. | 204/195 S |
| 4,121,988 | 10/1978 | Sano et al. | 204/195 S |
| 4,145,272 | 3/1979 | Nakamura et al. | 204/195 S |

FOREIGN PATENT DOCUMENTS 2738882  2/1978  Fed. Rep. of Germany ....... 204/195 S Primary Examiner—G. L. Kaplan
Attorney, Agent, or Firm—Cushman, Darby & Cushman

[57] ABSTRACT

An oxygen sensor having an oxygen-ion-conductive element made of a metal oxide with an outer electrode composed of three layers, one of which is the thinnest, second of which is the intermediate in thickness and the third of which is the thickest. This oxygen sensor maintains quick response characteristics over a long period of time.

6 Claims, 6 Drawing Figures

OXYGEN SENSOR

BACKGROUND OF THE INVENTION

The present invention relates to an oxygen sensor to be used with a device mounted on an automobile to reduce harmful exhaust emissions, and more particularly to an improved electrode therefor.

In a conventional oxygen sensor, there is provided an element which is shaped like a cup open at one end and made of metal oxides capable of conducting oxygen ions. Electrodes are formed on both inner and outer surfaces of the element to take out the electromotive force produced between those electrodes. It is well known that the thickness of the electrode closely relates to response characteristics of the sensor to changing gaseous circumstances and of course to the durability. When the porosity is the same, a thinner electrode reacts more quickly than a thicker one, since the exhaust gas reaches the element faster, therefore the response characteristics are better in thinner ones. On the other hand, thicker electrodes are advantageous as to wear and peeling-off, thus better in durability.

Taking the above facts into account, the thickness of the outer electrode was selected in the past to be about $1\mu$ to balance both response and durability requirements, however it did not satisfy the both requirements very well.

According to applicants' study, it was found that the response time improves or becomes faster after long time use, even if the thickness of the electrode is thicker. This is because the particles forming the electrode become larger after long time use, since the metal paricles collect and become sintered together. Applicants confirmed this phenomenon by an electron microscope. Applicants also found that the above sintering phenomenon takes place faster in a thinner electrode than in a thicker electrode.

SUMMARY OF THE INVENTION

In an oxygen electrode of the present invention, thinner and thicker portions are formed on the element, and further the porosity of the thinner portion is made the same or larger than the porosity of the thicker portion. Therefore the thinner portion which is quick in response characteristics works first, and then the thicker portion which also becomes fast in response after becoming more porous works secondly. Consequently the oxygen sensor of this type satisfies both quick response characteristics and high durability, and the performance of which does not change over a long period of time.

DETAILED DESCRIPTION OF PREFERRED EMBODIMENTS

Figure 1:
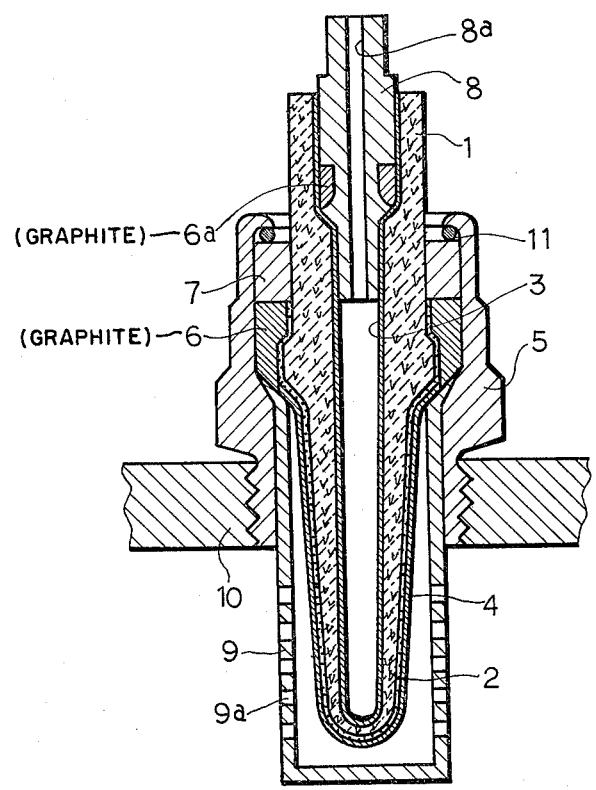
FIG. 1 shows a cross sectional view of an embodiment of the present invention.

In FIG. 1, numeral 1 designates an element mainly made of metal oxide capable of conducting oxygen ions, such as $ZrO_2$, $ThO_2$, $CeO_2$ and the like. 70~97 mol % of one of the above metal oxides and 30~3 mol % of one of other metal oxides, such as CaO and $Y_2O_3$ are mixed and then sintered to obtain the above element. An example of making the element is as follows. 90 mol % of $ZrO_2$ and 10 mol % of $Y_2O_3$ are mixed and pulverized to apply it to the preliminary firing, then it is shaped like a cup with one open end, after that the cup shaped element is fired at 1600° C.~1750° C. to obtain a fine sintered body. The outer surface of this element 1 is coated with Pt chemically first, an then coated electrically or by vacuum evaporation or by firing the paste on the element. This outer surface which is a first electrode 2 is subjected to the exhaust gas in the engine exhaust gas piep 10. The inner surface on the other hand is coated with Pt also chemically or by firing the paste put on the surface to obtain a second electrode 3. This electrode 3 makes a contact with the atmosphere.

Figure 2:
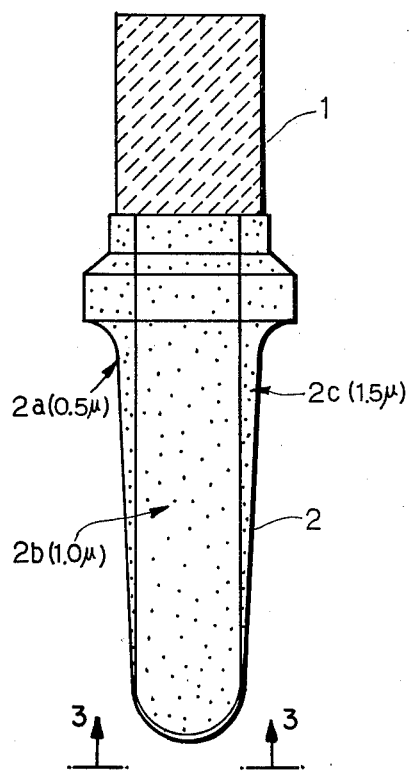
FIG. 2 shows a side view of the first embodiment of the main element of the present invention.
Figure 3:
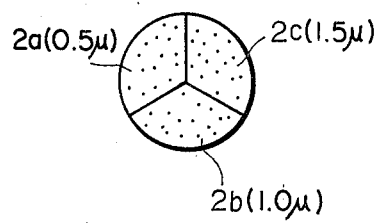
FIG. 3 shows a bottom view of the element shown in FIG. 2.

The first electrode 2 has three equally longitudinally divided portions 2a, 2b and 2c as shown in FIGS. 2 and 3. The thickness of the portions 2a, 2b and 2c are $0.5\mu$, $1.0\mu$ and $1.5\mu$ respectively and the porosity of these portions is the same in this embodiment. When making these three different layers, a $0.5\mu$ Pt chemical coating is made first, covering the entire outer surface of the element. Then another $0.5\mu$ electrical coating is made, masking the portion 2a, after that a second $0.5\mu$ electrical coating, which is the third coating as a whole, is made, masking the portions 2a and 2b. Consequently the portion 2b is coated twice to be $1.0\mu$ thick and the portion 2c is coated three times repeatedly to be $1.5\mu$ thick, thus making three different thickness layers. The film 4 on the electrode 2 is porous and put there to protect the electrode 2 and to stabilize the output. The film 4 is made of a temperature-resistive metal oxide, such as $MgO.Al_2O_3$ (Spinel), $ZrO_2$, $Al_2O_3$ or the like, and coated on the electrode 2 by dipping or by injection of plasma. Electrode-conductive metal housing 5 is used to fix the sensor to the exhaust pipe 10. An electro-conductive graphite ring 6 is put between the housing 5 and element 1 to be pressed down by an O ring 7. Another electro-conductive graphite ring 6a is also put between the element 1 and the stem 8. The stem 8 has a center hole 8a to introduce the atmosphere into the inner area of the element 2. A ring 11 is used to be fixed to finally make up the oxygen sensor. The housing 5 is electrically connected with the electrode 2 via the graphite ring 6, and the stem 8 is also electrically connected with the electrode 3 through another graphite ring 6a, thereby making terminals to take out the electromotive force. There is provided a protector 9 with small holes 9a to prevent a direct impingement of exhaust gas against the element 2.

Figure 5:
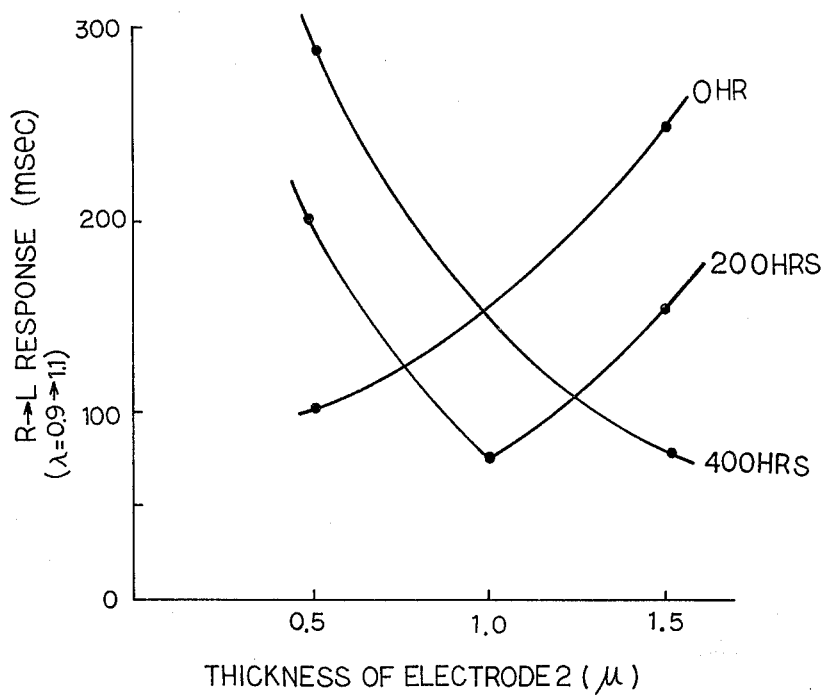
FIGS. 5 and 6 show graphs to be used in the explanatory portion of the present invention.

FIG. 5 shows that the thinner the electrode 2 is, the better the response time is, and the thicker the electrode is, the higher the durability is, when the porosity remains the same and when it is new. FIG. 5 also shows that the older electrodes demonstrate better response characteristics temporarily, i.e. the one of intermediate thickness shows quick response, and then the performance becomes poor again as the thickness increases. As to the oldest ones, the response characteristic is reverse with respect to the characteristic of new ones as shown in FIG. 5.

The oxygen sensor above constructed works as follows. The portion 2a which is $0.5\mu$ thick works first when new, since it is the one which demonstrates the fastest response, then the portion 2a becomes nonoperable because of its increased porosity which results in nonconductivity. However by this time the portion 2b starts to have more porosity, thus showing better response characteristics. Therefore this portion 2b works to detect the oxygen concentration at the fastest response time. As in the portion 2a, this portion 2b also becomes unworkable after some period of use. Then the third portion 2c is substituted for the portion 2b to become an active sensing place.

As above described, the oxygen sensor of the present invention selects the best portion to take the signal out at all times, thereby demonstrating the fastest response characteristics always for a long time.

Figure 6:
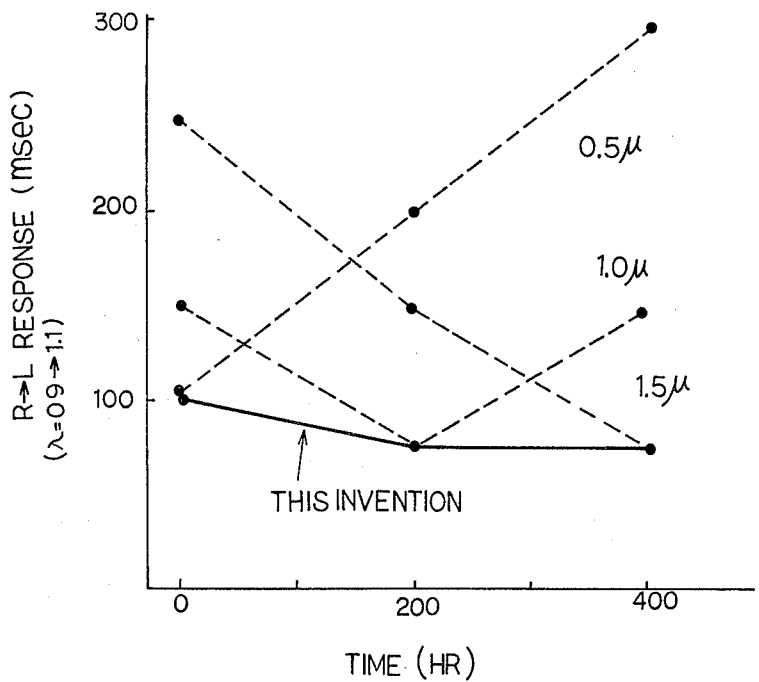

FIG. 6 shows the test data actually taken. The engine used is a 4-cylinder, 2000 cc engine, which is controlled to run at 4000 r.p.m.. The oxygen sensor was put into exhaust gas which is 850° C. and consists of 3% deoxidizing gas. The sensor was subjected to the exhaust gas for 400 hours in total. In the meantime, the sensor was taken out once in every 100 hours to measure the response time. Two kinds of model gas of air numbers 0.9 and 1.1 were used to switch the gas of air number 0.9 to the gas of air number 1.1 to take the measurement of the response time. In FIGS. 5 and 6, R means a gas of air number $\lambda=0.9$, and L means a gas of air number $\lambda=1.1$.

FIG. 6 shows that the oxygen sensor of the present invention demonstrates the best response time characteristics. The solid line shows the performance of the sensor of the present invention, and the broken lines show the performance of different thickness electrodes when singularly used. It also shows that the performance of the sensor of the present invention at 400 hours for example is better than that of the initial condition.

Figure 4:
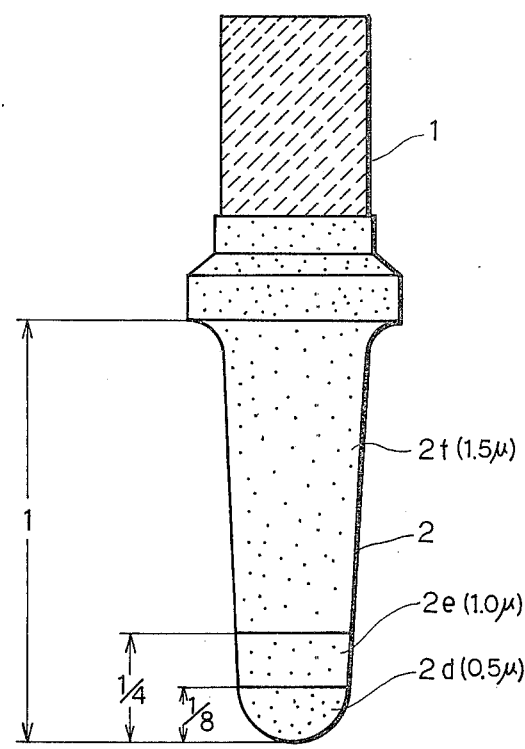
FIG. 4 shows a side view of the second embodiment of the main element of the present invention.

FIG. 4 shows another embodiment of the present invention. As shown there, the thickness changes from bottom to top. $0.5\mu$ thick portion 2d is formed at the lowest portion of the element 2, $1.0\mu$ portion 2e at the next, and $1.5\mu$ portion 2f at the above of the portion 2e.

The width of each of the portions 2d, 2e and 2f are as shown in FIG. 4. The method to make the portions $2d \sim 2f$ is the same as explained with respect to the first embodiment.

Following variations are also within the present invention.

The element 2 can be of a plate instead of a cup. In this case the thinner portion should be formed around the outmost edge of the plate, the next thinner portion at the inner portion of the above, and the thicker portion at the innermost area of the plate.

In the above embodiments, three different thickness portions are formed on the element, however simply two or more will work and satisfy the object of the present invention.

Although the portions $2a \sim 2f$ have $0.5\mu$ difference in thickness with each other, this $0.5\mu$ thickness can be of any other thickness.

Although the porosity of the portions $2a \sim 2c$ and $2d \sim 2f$ are the same, it may be different as well. For example the porosity of the thinner portion may be made larger than that of the thicker portion, since if the porosity of the thicker portion is larger than that of the thinner portion, the thicker portion works first, which is not desirable.

Moreover the thickness of the film 4 can be changed to put a thinner film on the thinner electrode and to put a thicker film onto the thicker electrode. Electrodes having this kind of film will demonstrate better response characteristics and higher durability. As to the porosity of this kind of film, the porosity of the thinner film should be selected to be equal or larger than that of the thicker film.

The material of Pt for the electrodes 2 and 3 can be substituted for Pt—Rh alloy, Pt—Pd alloy or Pd. Of course the oxygen sensor of this type can be also use for other purposes than purifying exhaust emission.

What is claimed is:

1. An oxygen sensor comprising an element made of a metal oxide, a first electrode coated on one surface of said element, and a second electrode coated on the other surface of said element, both of said coatings independently being platinum, a platinum alloy or palladium, wherein said second electrode is composed of a plurality of portions, one of which is about $0.5\mu$ thick and forms the thinnest portion, and said portions including said thinnest portion having a thickness gradually increasing by increments of about $0.5\mu$ from said thinnest portion.

2. An oxygen sensor comprising a cup-shaped element made of a metal oxide capable of conducting oxygen ions to produce electromotive force therein,
   an inner electrode coated on an inner surface of said element,
   an outer electrode coated on an outer surface of said element to take out said electromotive force therefrom each of said inner and outer electrode coatings independently being platinum, a platinum alloy or palladium, and
   a porous film coated on said outer electrode to protect said outer electrode,
   wherein said outer electrode consists of three circumferential layers, the first of said layers being the thinnest, positioned at the bottom of said element and having a thickness of about 0.5 microns, the second layer adjacent said first layer of an intermediate thickness of about 1.0 microns, and a third layer being positioned close to an open end of said cup-shaped element and adjacent to said second layer being the thickest layer having a thickness of about 1.5 microns, said first, second and third layers covering all the effective area of said outer surface of said element.

3. An oxygen sensor as claimed in claim 2 wherein said first portion is a predetermined length X of said second electrode, said second portion is about ¼ X at the lower end of said second electrode and said third portion is about ⅛ X at the lower most portion of said electrode.

4. An oxygen sensor as claimed in claim 2 wherein each of said first, second and third layers are substantially equal to each other in porosity.

5. An oxygen sensor having an element with a first and second surface made of a metal oxide capable of conducting oxygen ions for detecting oxygen concentration in a gas, said sensor comprising:
   a first electrode having platinum, a platinum alloy or palladium coated on the first surface of said element,
   a second electrode having platinum, a platinum alloy or palladium coated on the second surface of said element for taking out the electromotive force produced between said first and second electrodes;
   said second electrode constituted by three substantially equal longitudinal portions each of which having different thicknesses of coating thereon, the first portion having a coating of about 0.5 microns, the second portion having a coating of about 1.0 microns and the third portion having a coating of about 1.5 microns, each of said portions defining a longitudinally defined area of said second surface to cover all the effective area of said second surface; and a porous protective film coated over the second electrode.

6. The oxygen sensor as claimed in claim 5 wherein each of said first, second and third layers are substantially equal to each other in porosity.

* * * * *